United States Patent
Clark

(10) Patent No.: US 11,364,015 B2
(45) Date of Patent: Jun. 21, 2022

(54) ULTRASONIC SHEAR WAVE IMAGING WITH BACKGROUND MOTION COMPENSATION

(71) Applicant: KONINKLIJKE PHILIPS N.V., Eindhoven (NL)

(72) Inventor: David Wesley Clark, Derry, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 373 days.

(21) Appl. No.: 16/334,792

(22) PCT Filed: Sep. 22, 2017

(86) PCT No.: PCT/IB2017/055756
§ 371 (c)(1),
(2) Date: Mar. 20, 2019

(87) PCT Pub. No.: WO2018/060820
PCT Pub. Date: Apr. 5, 2018

(65) Prior Publication Data
US 2019/0231320 A1 Aug. 1, 2019

Related U.S. Application Data

(60) Provisional application No. 62/401,268, filed on Sep. 29, 2016.

(51) Int. Cl.
*A61B 8/08* (2006.01)
*A61B 8/14* (2006.01)
(Continued)

(52) U.S. Cl.
CPC ............. *A61B 8/5276* (2013.01); *A61B 8/14* (2013.01); *A61B 8/4488* (2013.01); *A61B 8/463* (2013.01);
(Continued)

(58) Field of Classification Search
CPC ....... A61B 8/5276; A61B 8/14; A61B 8/4488; A61B 8/463; A61B 8/485; G01S 7/52095;
(Continued)

(56) References Cited

U.S. PATENT DOCUMENTS 4,644,795 A   2/1987 Augustine
5,318,033 A   6/1994 Savord
(Continued)

FOREIGN PATENT DOCUMENTS

| EP | 2294448 B1 * | 3/2016 | ......... G01S 7/52077 |
| WO | WO-2007030016 A1 * | 3/2007 | ......... G01S 7/52049 |
| WO | 2009140607 A1 | 11/2009 | |

OTHER PUBLICATIONS

MaAleavey et al., "Validation of SMURF Estimation of Shear Modulus in Hydrogels" Ultrasonic Imaging 31, 131-150 (2009) (Year: 2009).*

(Continued)

*Primary Examiner* — Boniface Ngathi N

(57) ABSTRACT

An ultrasonic diagnostic imaging for analyzing shear wave characteristics utilizes a background motion compensation subsystem which acts as a spatial filter of pulse-to-pulse autocorrelation phases over the ROI of tracking pulse vectors to compensate for background motion. The subsystem is configured to compute the sum of all lag-1 autocorrelations of tracking line ensemble data over the tracking ROI, for each PRI. The inventive technique does not significantly reduce sensitivity to shear waves, because the shear wave is spatially smaller than the ROI.

15 Claims, 4 Drawing Sheets

(51) Int. Cl.
*A61B 8/00* (2006.01)
*G01S 7/52* (2006.01)
*G01S 15/89* (2006.01)

(52) U.S. Cl.
CPC .......... *A61B 8/485* (2013.01); *G01S 7/52022* (2013.01); *G01S 7/52031* (2013.01); *G01S 7/52042* (2013.01); *G01S 7/52085* (2013.01); *G01S 7/52095* (2013.01); *G01S 15/8915* (2013.01); *G01S 15/8981* (2013.01)

(58) Field of Classification Search
CPC .............. G01S 7/52022; G01S 7/52085; G01S 7/52031; G01S 7/52042; G01S 15/5915; G01S 15/5981
See application file for complete search history.

(56) References Cited

U.S. PATENT DOCUMENTS

| | | | |
|---|---|---|---|
| 5,345,426 | A | 9/1994 | Lipschutz |
| 5,469,851 | A | 11/1995 | Lipschutz |
| 5,606,971 | A | 3/1997 | Sarvazyan |
| 5,810,731 | A | 9/1998 | Sarvazyan et al. |
| 6,494,838 | B2 | 12/2002 | Cooley et al. |
| 6,695,783 | B2 | 2/2004 | Henderson et al. |
| 7,252,004 | B2 | 8/2007 | Fink |
| 8,753,277 | B2 | 6/2014 | Mcaleavey |
| 9,964,634 | B2 | 5/2018 | Nikolov et al. |
| 2003/0131511 | A1 | 7/2003 | Lai |
| 2006/0052699 | A1* | 3/2006 | Angelsen ............... A61B 8/483 600/437 |
| 2011/0184287 | A1* | 7/2011 | McAleavey ........... A61B 8/485 600/438 |
| 2012/0134233 | A1* | 5/2012 | Lin ..................... G01S 7/52046 367/7 |
| 2013/0028536 | A1* | 1/2013 | Hazard ................ A61B 8/5276 382/275 |
| 2013/0296698 | A1* | 11/2013 | Fraser ................ G01S 7/52036 600/438 |
| 2013/0336560 | A1* | 12/2013 | Wong .................. A61B 8/5207 382/131 |
| 2015/0133783 | A1* | 5/2015 | Tabaru ................ A61B 8/5223 600/438 |
| 2015/0272547 | A1* | 10/2015 | Freiburger ............... A61B 8/54 600/438 |
| 2016/0183926 | A1* | 6/2016 | Asami .................... A61B 8/461 600/437 |
| 2017/0333005 | A1 | 11/2017 | Chen et al. |

OTHER PUBLICATIONS

Urban et al. "Error in Estimates of Tissue Material Properties From Shear Wave Dispersion Ultrasound Vibrometry" IEEE Trans. UFFC, vol. 56, No. 4, (Apr. 2009).

Christopher Hazard et al. "Integration of Crawling Waves in an Ultrasound Imaging System.." System and Design Considerations Ultrasound in Medicine and Biology, vol. 38, No. 2, Oct. 29, 2011, p. 296-311.

Deng Yufeng et al. "Ultrasonic Shear Wave Elasticity Imaging Sequencing and Data Processor Using a Verasonics Research Scanner" IEEE Trans. on Ultrasonics , Ferroelectrics and Frequency Control, vol. 64, No. 1, Jan. 1, 2017, p. 164-176.

Fahey et al. "The Impact of Physiological Motion on Tissue Tracking During Radiation Force Imaging" Ultrasound in Med. and Biol. vol. 33, No. 7, Jul. 1, 2007 p. 1149-1166.

Bjaerum et al. "Clutter Filters Adapted to Tissue Motion in Ultrasound Color Flow Imaging" IEEE Transactions on Ultrasonics, Ferroelectrics and Frequency Control, vol. 49, No. 6, Jun. 2002 p. 693-704.

\* cited by examiner

ULTRASONIC SHEAR WAVE IMAGING WITH BACKGROUND MOTION COMPENSATION

CROSS-REFERENCE TO PRIOR APPLICATIONS

This application is the U.S. National Phase application under 35 U.S.C. § 371 of International Application No. PCT/IB2017/055756, filed on Sep. 22, 2017, which claims the benefit of U.S. patent application Ser. No. U.S. 62/401,268, filed on Sep. 29, 2016. These applications are hereby incorporated by reference herein.

This invention relates to medical diagnostic ultrasound systems and, in particular, to ultrasound systems which perform measurements of tissue stiffness or elasticity using shear waves.

One of the long-sought goals of diagnostic imaging is precise tissue characterization. A clinician would like to scan a diagnostic region of an organ of the body and have the imaging system identify the characteristics of the tissue in the image. Ideally, the clinician would like the imaging system to identify a lesion as malignant or benign. While fully realizing this objective remains yet to be accomplished, diagnostic imaging can nonetheless give the clinician clues as to the makeup of tissue. One technique in this area is elastography, which measures the elasticity or stiffness of tissues in the body. For example, breast tumors or masses with high stiffness might be malignant, whereas softer and more compliant masses are likely to be benign. Since the stiffness of a mass is known to correlate with malignancy or benignity, elastography provides the clinician with another piece of evidence to aid in diagnosis and determination of a treatment regimen.

One approach to elasticity measurement is shear wave measurement. When a point on the body is compressed, then released, the underlying tissue undergoes local axial displacement in the direction of the compression vector, then rebounds back up when the compressive force is released. But since the tissue under the compressive force is continuously joined to surrounding tissue, the uncompressed tissue lateral of the force vector will respond to the up-and-down movement of the local axial displacement. A rippling effect in this lateral direction, referred to as a shear wave, is the response in the surrounding tissue to the downward compressive force. Furthermore, it has been determined that the force needed to push the tissue downward can be produced by the radiation pressure from an ultrasound pulse, and ultrasound reception can be used to sense and measure the tissue motion induced by the shear waves. Shear wave velocity is determined by local tissue mechanical properties. The shear wave will travel at one velocity through soft tissue, and at another, higher velocity through hard tissue. By measuring the velocity of the shear wave at a point in the body, information is obtained as to characteristics of the tissue such as its shear elasticity modulus and Young's modulus. The laterally propagating shear wave travels slowly, usually a few meters per second or less, making the shear wave susceptible to detection, although it attenuates rapidly over a few centimeters or less. See, for example, U.S. Pat. No. 5,606,971 (Sarvazyan) and U.S. Pat. No. 5,810,731 (Sarvazyan et al.) Estimates of the shear wave velocity are virtually independent of the amplitude of tissue displacement and tissue density normally has little variance, which make the technique suitable for objective quantification of tissue characteristics with ultrasound.

In conventional pulse-echo ultrasound, an ultrasound pulse is transmitted out from the probe and echoes scattered back from tissue encountered by the pulse are received directly. However, since the shear wave travels laterally, it cannot be directly received by the transmitting transducer and its frequency, typically several hundred Hertz, is much lower than that of imaging ultrasound frequencies. A solution to this problem has been suggested by Fink et al. in U.S. Pat. No. 7,252,004, who propose to observe the propagation of the shear wave by rapidly acquiring images from unfocused plane waves, each insonifying a large expanse of tissue and repeated at a rate of at least 500 repetitions per second, and preferably in the range of 1000 to 5000 repetitions per second. Rather than acquire an image by transmitting and receiving individual lines of data across the image field, which entails a full transmit-receive cycle for each line, Fink et al. insonify the entire region of interest (ROI) with a single unfocused wave, then acquire echoes resulting from the wave transmission through the tissue during a subsequent reception period. Since each interrogation of the ROI only requires a single wave transmission, data sets can be successively acquired at the high rate that Fink et al. desire. While the unfocused wave lacks both the signal-to-noise performance and the focal resolution of individual image lines, Fink et al. intend to offset this deficiency with their high rate of data acquisition. It would be desirable, however, to be able to observe and measure the propagation velocity of a shear wave with precision and good signal-to-noise performance and to do so with focused image lines rather than unfocused plane waves.

A diagnostic ultrasonic imaging system which measures shear wave velocity with focused received lines called tracking lines is described in U.S. pat. pub. no. 2013/0131511 (Peterson et al.) One or more push pulses are transmitted into tissue with an ultrasound probe to ultrasonically compress the tissue in the vectorial direction of the push pulses. Immediately thereafter, focused tracking pulses are transmitted and received by the probe in the vicinity of the push pulse vector which generates the shear wave. Each tracking pulse vector is repetitively sampled in a time-interleaved manner so that motion produced by a shear wave can be detected when it occurs at each tracking pulse vector location, preferably by correlating the echo data from successive interrogations of the vector. As the shear wave moves laterally away from the push pulse vector, the positioning of the tracking pulses can also be moved laterally to follow the propagation of the shear wave. The data from the repetitively sampled tracking pulse vectors is processed to find the times at which the shear wave causes a peak displacement at each point of the tracking pulse vector, preferably by cross-correlation, curve-fitting or interpolating successive displacement measurements. Analysis of the times at which points on adjacent sampling vectors experience peak displacement produces a measurement corresponding to the velocity of the shear wave at particular vector locations, with velocity variations indicating tissues of different stiffness or elasticity. Since the shear waves attenuate rapidly, it is generally not possible to acquire shear wave data from an entire image field with a single push pulse vector. Thus, the process is repeated at another location in the tissue to acquire shear wave velocity measurements at another region of the tissue. The process is repeated until shear wave data has been acquired over the desired image field. The velocity information is preferably presented as a two- or three-dimensional image of the tissue, color-coded by the shear wave velocity data at points in the image.

The tissue motion caused by shear wave travel is very subtle, however. Peak shear wave tissue displacements are at best about 10 µm, and under more common, less favorable circumstances are closer to 1 µm. The precision of displacement estimates for accurate shear wave measurements should be at least on the order of 100 nm. Thus, the tissue displacement resulting from shear wave travel can easily be overwhelmed by background motion due to patient heartbeat and hand-held transducer movement, even with patients who are able to hold their breath during the procedure. Prior shear wave detection algorithms have used various forms of temporal high-pass filtering of displacement, such as linear drift subtraction (detrending) and frequency-domain Butterworth high pass filtering to attenuate background motion. But this inevitably requires a compromise between background motion suppression and low velocity shear wave sensitivity. It would be desirable to be able to compensate for background motion effects without reducing shear wave detection sensitivity.

A system which compensates for background motion during shear wave measurement is described in U.S. pat. pub. no. 2013/0296698 (Fraser et al.) The shear wave imaging system described in this publication transmits additional tracking pulses in surrounding tissue to detect the presence of relative motion between the ultrasound probe and the ROI where shear waves are detected. When background motion is sensed, the measured shear wave characteristics are compensated for its effect. This technique, however requires the use of additional tracking pulses to sample background motion, using time that could be better spent tracking the shear wave displacement, e.g., by acquiring longer ensembles of echo signals from along the shear wave tracking vectors. Accordingly, it would be desirable to be able to compensate for background motion effects during shear wave measurement without the need to transmit and acquire additional signals and echoes that are directed specifically to background motion sensing.

In accordance with the principles of the present invention, an ultrasonic shear wave measurement system is described which compensates for the effects of background motion by use of a spatial high pass filtering technique which filters the pulse-to-pulse phases of echo ensemble autocorrelation. A preferred implementation performs the spatial filtering by performing complex autocorrelation of tracking pulse echo signals for the phase shift averaged over the region of interest where the tracking pulses are being transmitted.

In the drawings:

FIG. 1 illustrates in block diagram form an ultrasonic diagnostic imaging system constructed to perform shear wave measurement.

FIG. 2 spatially illustrates a sequence of pulse pulses along a push pulse vector, the resultant shear wavefront, and a series of tracking pulse vectors.

Figure 1:
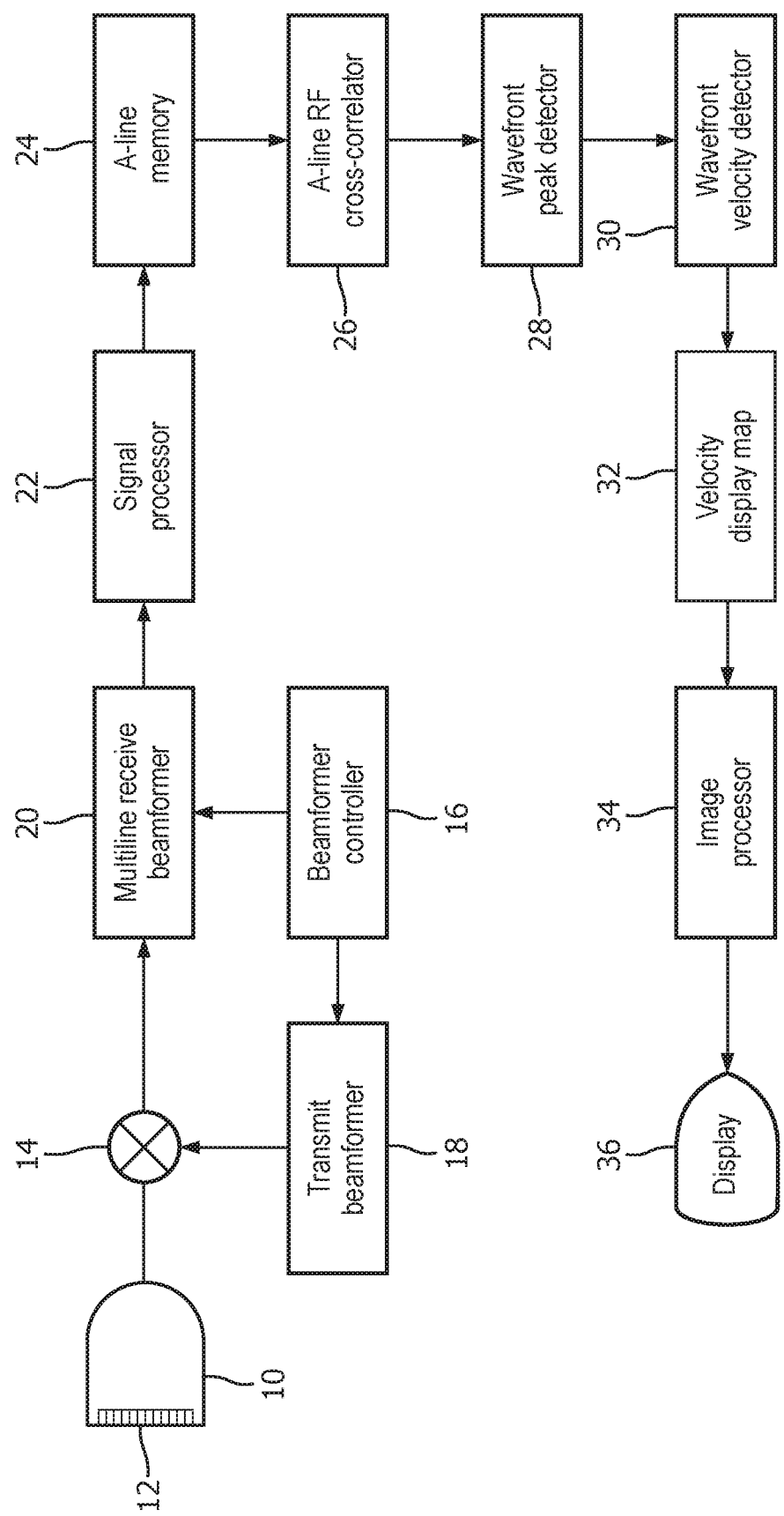

Referring first to FIG. 1, an ultrasound system constructed for the measurement of shear waves is shown in block diagram form. An ultrasound probe 10 has an array 12 of transducer elements for transmitting and receiving ultrasound signals. The array can be a one dimensional or a two-dimensional array of transducer elements. Either type of array can scan a 2D plane and a two-dimensional array can be used to scan a volumetric region in front of the array. The array elements are coupled to a transmit beamformer 18 and a multiline receive beamformer 20 by a transmit/receive (T/R) switch 14. Coordination of transmission and reception by the beamformers is controlled by a beamformer controller 16. The multiline receive beamformer produces multiple, spatially distinct receive lines (A-lines) of echo signals during a single transmit-receive interval. The echo signals are processed by filtering, noise reduction, and the like by a signal processor 22, then stored in an A-line memory 24. Temporally distinct A-line samples relating to the same spatial vector location are associated with each other in an ensemble of echoes relating to a common point in the image field. In a typical shear wave measurement system, the r.f. echo signals of successive A-line sampling of the same spatial vector are cross-correlated by an A-line r.f. cross-correlator 26 to produce a sequence of samples of tissue displacement for each sampling point on the vector. Alternatively, the A-lines of a spatial vector can be Doppler processed to detect shear wave motion along the vector, or other phase-sensitive techniques can be employed. A wavefront peak detector 28 is responsive to detection of the shear wave displacement along the A-line vector to detect the peak of the shear wave displacement at each sampling point on the A-line. In a preferred embodiment this is done by curve-fitting, although cross-correlation and other interpolative techniques can also be employed if desired. The time at which the peak of the shear wave displacement occurs on an A-line is noted in relation to the times of the same event at other A-line locations, all to a common time reference, and this information is coupled to a wavefront velocity detector 30 which differentially calculates the shear wave velocity from the peak displacement times on adjacent A-lines. This velocity information is coupled into a velocity display map 32 which indicates the velocity of the shear wave at spatially different points in a 2D or 3D image field. The velocity display map is coupled to an image processor 34 which processes the velocity map, preferably overlaying the velocity map on an anatomical (B mode) ultrasound image of the tissue, for display on an image display 36.

Figure 2:
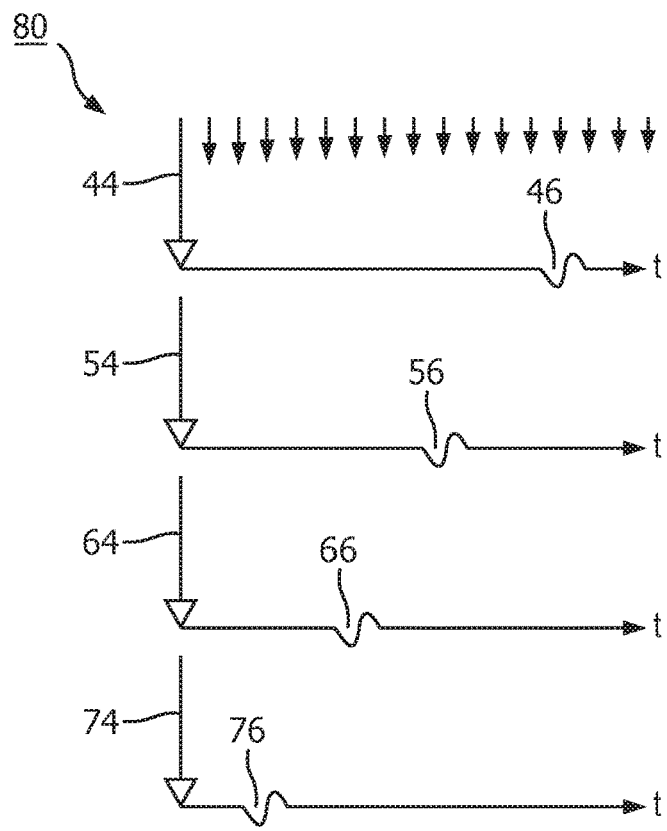

FIG. 2 is an illustration of the use of four push pulses to create a composite shear wavefront. The four push pulses are transmitted along vectors 44, 54, 64 and 74 which are seen to be aligned along a single vectorial direction in FIG. 2. When the shallowest push pulse of vector 44 is transmitted first, followed by successively deeper push pulses, the shear wavefronts of the respective push pulses will have propagated as indicated by waves 46, 56, 66, and 76 by a time shortly after the last push pulse (vector 74) has been transmitted. As the shear waves 46, 56, 66, and 76 travel outward from the push pulse vector, they are interrogated by tracking pulses 80 shown in spatial sequence along the top of the drawing. Tracking pulses can occur between as well as after push pulses.

Figure 3:
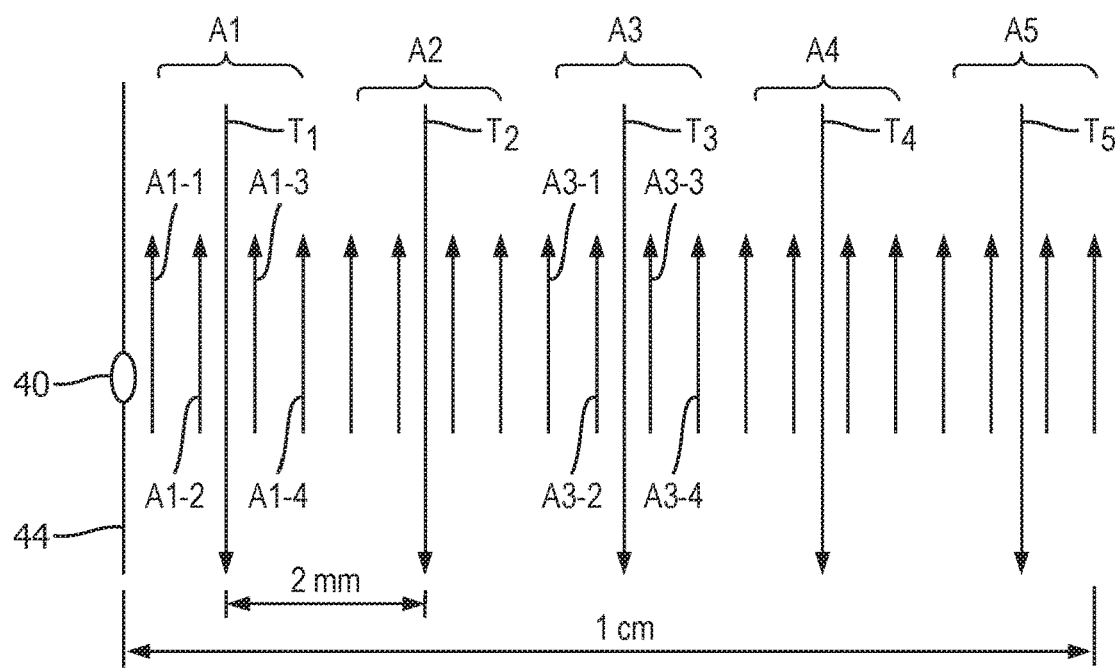
FIG. 3 illustrates four laterally adjacent groups of 4× multiline tracking pulse vectors.

The velocity of the laterally traveling shear wave is detected by sensing the tissue displacement caused by the shear wave as it proceeds through the tissue. This is done with time-interleaved sampling pulses transmitted adjacent to the push pulse vector as shown in FIG. 3. In this example the push pulse(s) 40 is transmitted along push pulse vector 44 to cause a laterally traveling shear wave. A-line vectors adjacent to the push pulse vector 40 are sampled by sampling pulses T1, T2, T3, T4, and T5 transmitted along each vector in a time-interleaved sequence. For example, the first vector location A1 is sampled by a first pulse T1, then the second vector location A2 by the next pulse T2, then A3, A4, and A5. Then vector location A1 is sampled again, and the sequence repeats at a pulse repetition frequency (PRF), and the interval between pulse transmissions is referred to as the pulse repetition interval (PRI). Since the sampling is time-interleaved, each of the five vector locations is sampled once in every five sampling pulses in this example. In this example every vector location is pulsed fifty-five times for a total tracking time of 27.5 msec. Each pulse results in echoes returning from along the vector which are sampled by a high speed A/D converter. Thus, for every sampled point along each vector there is an ensemble of 55 samples, with each sample taken at one-fifth the pulse rate of the T1-T5 sampling pulse sequence. The typical ensemble length at each echo location on a sampling vector is 40-100 samples. The sampling rate will be chosen in consideration of the frequency content of the shear wave displacement being detected so as to satisfy the Nyquist criterion for sampling. Since the purpose of the sampling is to sense and track the displacement effect of the shear wave as it progresses through the tissue, the vector locations may be located closer together for slowly moving shear waves and further apart for more rapidly moving shear waves. Other sequences of time-interleaving the vector sampling may also be employed. For example, odd-numbered vectors could be sampled in sequence, followed by sampling of the even-numbered vectors. As another example, vector locations A1-A3 could be sampled in a time-interleaved manner, then vector locations A2-A4, then vector locations A3-A5 to track the shear wave displacement as it progresses. Other sequences may also be employed based upon the exigencies of the situation. The ensembles of time-interleaved samples at each point along each sampling vector are then processed to find the time of peak tissue displacement at each point of each vector as described in detail below.

Figure 4:
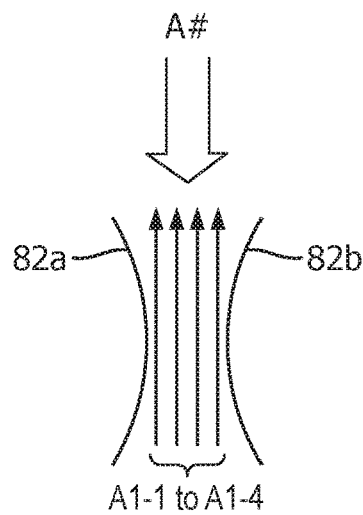
FIG. 4 illustrates the transmission and reception of 4× multiline for the production of four adjacent multiline tracking pulse vectors in a region of interest.

In accordance with a further aspect of the present invention, multiline transmission and reception is employed so that a single tracking pulse can simultaneously sample a plurality of adjacent, tightly spaced, A-line locations. Referring to FIG. 4, one technique for multiline transmission and reception is shown. In FIG. 4 a single A-line tracking pulse with a beam profile 82a, 82b which insonifies multiple receive line locations is transmitted as indicated by the wide arrow A#. Preferably the tracking pulse is a so-called "fat pulse" as described in U.S. Pat. No. 4,644,795 (Augustine), for example. In this example four receive line locations A1-1, A1-2, A1-3 and A1-4 are insonified. Echoes from the four receive lines (4× multiline) are received in response to the single transmit pulse and are appropriately delayed and summed to produce coherent echo signals along each of the receive lines. Beamformer capable of producing such simultaneous multilines are described, for instance, in U.S. Pat. No. 5,318,033 (Savord), U.S. Pat. No. 5,345,426 (Lipschutz), U.S. Pat. No. 5,469,851 (Lipschutz), and U.S. Pat. No. 6,695,783 (Henderson et al.) These multiline beamformers are typically used to decrease the acquisition time and thereby increase the frame rate of live ultrasound images, which is particularly useful when imaging the beating heart and blood flow in real time echocardiography. They are also useful in 3D ultrasound imaging so that real time frame rates of display can be attained. See, in this regard, U.S. Pat. No. 6,494,838 (Cooley et al.) In an implementation of the present invention, the benefit of multiline acquisition is two-fold: it enables a closely-spaced sampling line density and rapid acquisition of a short duration shear wave which only travels a short distance through tissue before being dissipated by attenuation. While higher order multiline may be employed which acquires samples along a greater number of A-lines at the same time and thus a higher sampling rate, this will require a broader transmit beam (A#) to simultaneously insonify the greater number of receive lines. The broader transmit beam will consequently diminish the signal-to-noise performance of the higher order implementation.

FIG. 3 illustrates the use of 4× multiline reception for transmission and reception along each sampling vector A1-A5. A first tracking pulse $T_1$ is transmitted close to the push pulse vector 44, insonifying four receive line locations A1-1 to A1-4 and four multiline A-lines are received in response from the lateral region A1. When the four multilines are centered with respect to the transmitted tracking pulse, echoes from two A-lines are received on each side of the center of the tracking pulse beam center, shown by A1-1 and A1-2 to the left of center and A1-3 and A1-4 to the right of center. In a preferred embodiment the A-lines are spaced 0.5 mm apart from each other. Shear waves generally move at a speed of 1-10 meters per second, and consequently tracking pulses are repetitively transmitted down regions A1-A5 in a time-interleaved manner and A-line samples received from the A-line locations during the time intervals between push pulses (when there are such intervals), and for 20 msec after the last push pulse, after which the shear wave has propagated out of the one centimeter A1-A5 sampling window. Since shear waves can have frequency components in the range of about 100 Hz to about 1000 Hz, sampling theory dictates that each A-line should have a sampling rate of 2 kHz. This results in a set (ensemble) of fifty-five A-line samplings of each sampling point on each multiline A-line.

In the example of FIG. 3, five tracking pulses, $T_1$-$T_5$, are transmitted over successive sampling windows A1-A5 adjacent to the push pulse vector 44 to sample the shear wave displacement effect as the wave propagates. A typical sampling pulse is a short pulse, usually only one or two cycles, at a frequency suitable for penetrating the depth being studied, such as 7-8 MHz. Each tracking pulse is offset by 2 mm from its adjacent neighbors, resulting in twenty A-lines spaced 0.5 mm apart with 4× multiline over a total distance of one centimeter. There are various ways the interrogate the sampling windows. One is to just sample region A1 until the shear wave is detected, then to begin sampling in region A2, then A3, and so on. Another is to time interleave the sampling in the regions as described above, sampling with tracking pulses $T_1$-$T_5$ in succession, then repeating the sequence. With the latter approach five sampling windows with twenty tracking A-line positions can track the shear wave effect simultaneously. After the shear wave has passed through the closest A1 sampling window and into the adjacent windows, sampling of the near window can be terminated and the sampling time can be devoted to the remaining sampling windows through which the shear wave is still propagating. Sampling continues until the shear wave has propagated out of the one cm. sampling region, by which time the shear wave has usually attenuated below a detectable level. Shear waves on average have a relaxation time of 10 msec.

It is necessary that the sampling times of the tracking A-line positions be related to a common time base when the tracking pulses are time-interleaved so that the results can be used to make a continuous measurement of time, and hence velocity, across the one cm. sampling region. For example, since the sampling pulses for sampling window A2 do not occur until 50 microseconds following the corresponding sampling pulses for window A1, a 50 microsecond time offset exists between the sampling times of the two adjacent windows. This time difference must be taken into account when comparing the peak times of displacement in the respective windows, and must be accounted for in an accumulated manner across the full one centimeter sampling window. Referencing the sampling times of each sampling vector to a common time reference can resolve the problem of the offset sampling times.

Figure 5:
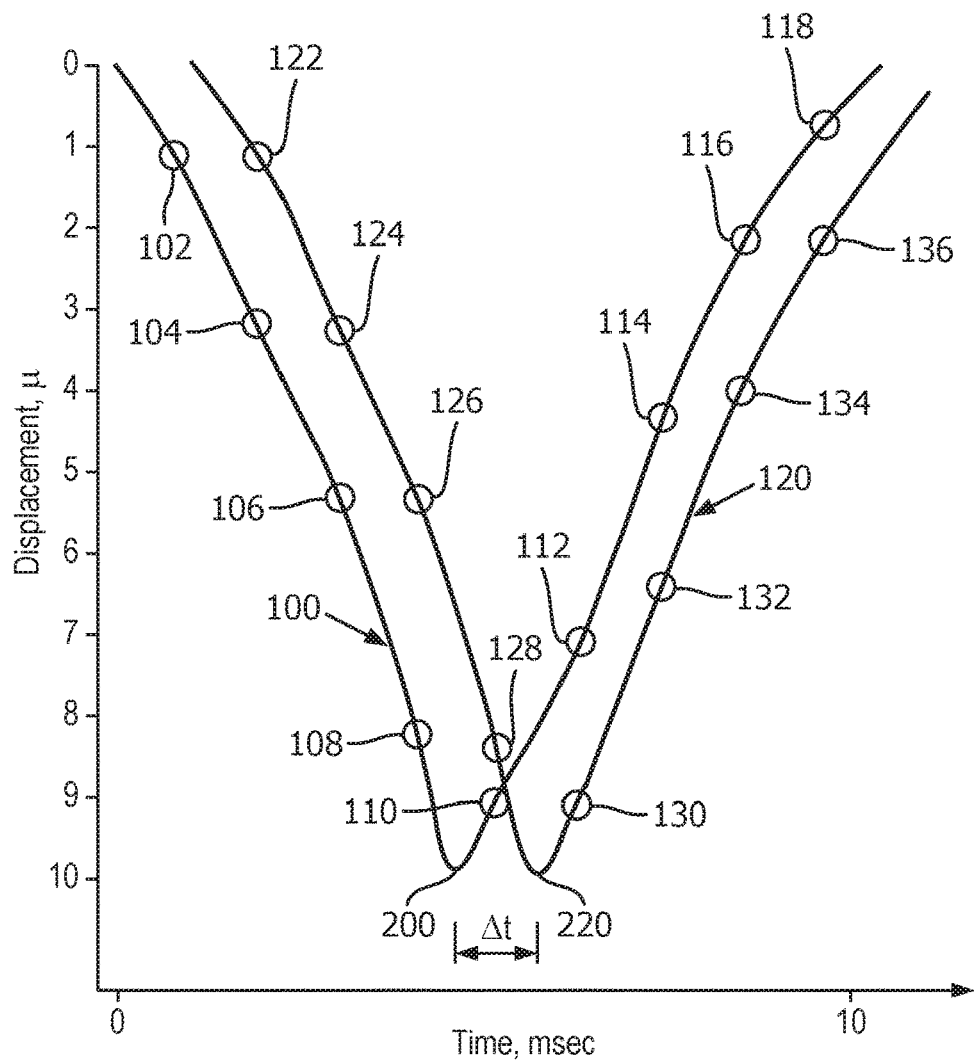
FIG. 5 illustrates shear wave displacement curves at two locations as it progresses through tissue.

Since a diagnostic region-of-interest (ROI) is generally greater than one centimeter in width, the procedure of FIG. 5 is repeated with push pulses transmitted at different lateral locations across the image field. An image field is thereby interrogated in one cm. wide regions, and the results of the regions are displayed adjacent to each other to present an image of the full ROI. In a preferred implementation a Philips Healthcare L12-5 probe is used, which has a 5 cm. aperture. A four cm. wide image field is interrogated in four adjacent or overlapping one cm. regions, which are then displayed side-by-side or wholly or partially overlaid on the display.

FIG. 5 illustrates a sequence of displacement values for two laterally adjacent points of tissue on two adjacent A-lines such as A1-3 and A1-4 in FIG. 3. Curve 100 represents the displacement over time caused by passage of a shear wave through a point on A-line A1-3, and curve 120 the displacement at an adjacent point of A-line A1-4. Points 102-118 of tissue displacement values are calculated from local cross correlations of r.f. data (e.g., 10-30 r.f. samples in depth) acquired around a sampling point depth on A1-3 over time to yield the local displacement values over time at the depth point. The points 102-118 of displacement values detected at successive times (y-axis), when plotted as a function of time, are joined to form the first displacement curve 100. At a point on second A-line A-1-4 spaced to the right of the point on the first A-line, the succession 122-136 of displacement values produced by local cross correlation can be joined to form a second displacement curve 120. Since the shear wave is traveling from left to right in this example, the second curve 120 for the right-most A-line is shifted to the right (in time) of the first displacement curve 100. A precise time reference of the passage of the wavefront from one point to the next is measured by the detected peak or inflection point of each displacement curve, indicated at 200 and 220 in this example. Various techniques can be used to find the curve peak. In one implementation the displacement values of each curve are processed by fitting curves to the values to form complete displacement curves 100, 120 and the curve peaks. Another technique is to interpolate additional points between the detected points to find the peak. Yet another technique is to determine the slopes of the curve on either side of the peak and determine the peak from the intersection of slope lines. Still another approach is cross-correlation of the curve data. When the peaks of the shear wave displacement at successive A-line positions are found by the waveform peak detector 28, their times of occurrence in relation to the detection of the points on the curves are noted. The difference of these times, Δt, taking into consideration sampling time offsets, and the spacing between the A-lines (e.g., 0.5 mm) can then be used by the wavefront velocity detector 30 to determine the velocity of the shear wave as it traveled between the two A-line locations. After the entire ROI has been interrogated in this manner and displacement curves and times of peak occurrence determined for each sample point on each A-line vector, the velocity of shear wave travel can be calculated from point to point across the entire region of interest. This two-dimensional matrix of velocity values is color-coded or otherwise coded in a display variation to form a velocity display map. The velocity display map is shown on the display 36, preferably overlaid and in spatial alignment with a B mode image of the region of interest.

As discussed above, the displacement of tissue due to propagation of a shear wave is very slight. The motion produced by acoustic radiation force (push pulse) transmission within diagnostic emission limits is very small, on the order of 0.1 to 15 micrometers in amplitude. The measurement of such tiny movement is accomplished by tracking the ultrasonic scattering from local inhomogeneities in the tissue being studied, which means that the received signal effects of a shear wave can be difficult to discriminate. In addition, shear wave motion is heavily damped in tissue, which is viscoelastic in character. Thus, an adequate signal-to-noise ratio is difficult to obtain, and penetration range is very limited. Any interfering signals will adversely affect the results. A significant source of interference is background motion, the relative motion of the transducer being used for the study and the region of tissue being studied. This can be caused by external sources such as unsteadiness of the operator's hand, or internal sources such as breathing, heartbeats, or other voluntary or involuntary movement of the subject. Prior art attempts at signal-to-noise improvement for acoustic radiation force techniques would bandpass filter the signals to eliminate the lower frequencies from the data. Most of the motion artifacts are below 50 Hz, so some improvement can be made by high pass filtering the received echo data. See, for example, Urban et al, "Error in Estimates of Tissue Material Properties from Shear Wave Dispersion Ultrasound Vibrometry," *IEEE Trans. UFFC*, vol. 56, No. 4, (Apr. 2009). However, some of this interference is quite large in amplitude, and bandpass or high pass filtering is not always sufficient to eliminate the adverse effects. Furthermore, the frequency of the desired tissue displacement often overlaps the frequency band being filtered out. Artifacts in the form of mis-estimated displacements and hence miscalculated shear wave velocities and moduli are common.

In accordance with the principles of the present invention, effects of background motion are compensated by spatially high pass filtering the pulse-to-pulse (PRI) autocorrelation phases of tracking pulse echo signal data. The following technique computes the sum of all lag-1 autocorrelations over the tracking ROI, for each PRI. This does not significantly reduce sensitivity to shear waves, because the shear wave is spatially smaller than the ROI. A preferred implementation for doing so is shown in block diagram form in FIG. 6. The background motion compensation subsystem shown in this drawing replaces the A-line cross-correlator 26 in the ultrasound system of FIG. 1, and operates every tracking pulse repetition interval. The signal processor 22 of FIG. 1 further includes a quadrature demodulator to produce the complex (I and Q) data used by the subsystem of FIG. 6. The complex (quadrature) r.f. or baseband tracking pulse echo data is in the form of s(z,x,nT), which is a function of axial dimension (depth) z, lateral dimension (tracking vector number) x, and slow time nT, where T is the pulse repetition interval at each spatial location on a tracking pulse vector from which an ensemble of echo signals of length n=0 to N has been received. A complex data multiplier 40 operates in the manner of an autocorrelator to perform a temporal lag-1 conjugate multiplication:

$$r(z,x,nT)=s(z,x,nT)*\text{conj}(s(z,x,nT-T))$$

for n=1 to N. The ensemble size of this complex multiplication is one less than the original data ensemble size due to the lag-1 offset. A summer 42 computes a spatial sum value from this result over the entire two-dimensional region of the ROI range of z and x:

$$q(nT)=\Sigma_z\Sigma_x r(z,x,nT)$$

This result is converted to a conjugate unit phasor value by a complex converter 46 which calculates:

$$q_1(nT) = \frac{conj(q(nT))}{|q(nT)|}$$

The previously calculated lag-1 data is multiplied with the conjugate unit phasor value by a multiplier 48 to compensate for background motion by calculating:

$$r_C(z,x,nT)=r(z, x, nT)*q_1(nT)$$

The axial displacement d of tissue along a tracking vector by a shear wave is proportional to the arc tangent of the background-compensated lag-1 complex data. That is, $$d(z,x,nT) \propto \text{angle}(r_C(z,x,nT))=\text{atan 2 }(\text{imag}(r_C(z,x,nT)), \text{real}(r_C(z,x,nT)))$$

This displacement, calculated by an arc tangent calculator 50 and thus estimated as the angle of the autocorrelation, may be further filtered if desired and used by the wavefront peak detector and velocity detector 28,30 to estimate the shear wave velocity.

The foregoing background motion compensation system and technique can also be used to produce motion-compensated data for blood flow detection. A multiplier 52 multiplies the input data s(z,x,nT) with a cumulative product of the compensation unit phasors by calculating:

$$s_C(z, x, 0) = s(z, x, 0)$$

$$s_C(z, x, nT) = s(z, x, nT) * \prod_{k=1}^{n} q_1(kT), \text{ for } n = 1 \text{ to } N$$

This result is coupled to a flow detection processor for measurement of blood flow, usually after ensemble high pass filtering or filtering by another type of clutter filter.

Figure 6:
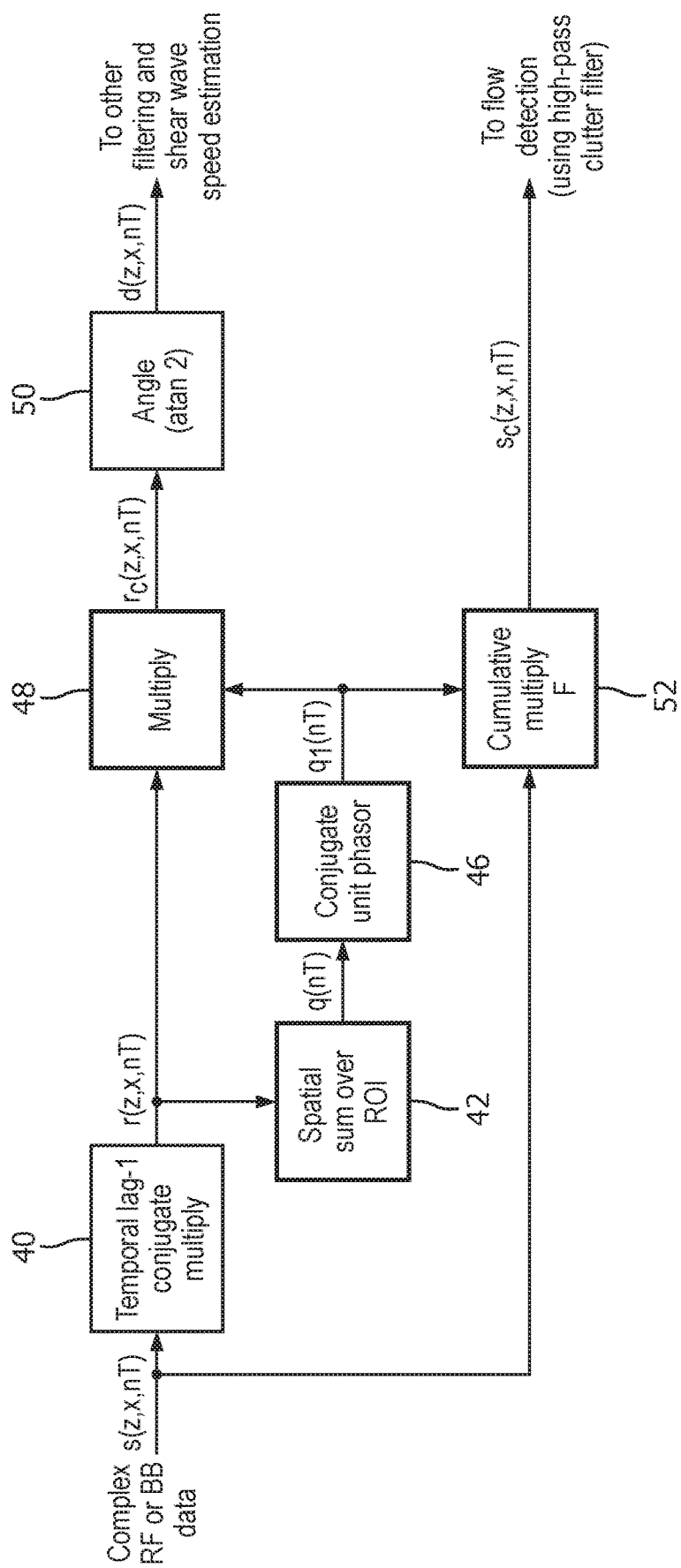
FIG. 6 illustrates in block diagram form a spatial high pass filtering system constructed in accordance with the principles of the present invention for compensating for the effects of background motion in a shear wave imaging system such as that of FIG. 1.

It should be noted that the ultrasound system which measures tissue displacement due to shear wave propagation and shear wave velocity of FIG. 1, and in particular the component structure of the background motion subsystem of FIG. 6 may be implemented in hardware, software or a combination thereof. The various embodiments and/or components of an ultrasound system, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory devices such as the A-line memory 24 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including the shear wave measurement and background motion compensation subsystem described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. For example, the equations calculated by the subsystem of FIG. 6 may be executed by software modules calculating the equations. The software also may include modular programming in the form of object-oriented programming. The processing of input data by the processing machine may be in response to operator commands, or in response to results of previous processing, or in response to a request made by another processing machine. In the background motion compensation subsystem of FIG. 6, for instance, software instructions are conventional employed to calculate the equations given above.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:
1. An ultrasonic diagnostic imaging system comprising:
an ultrasonic array probe,
wherein the ultrasonic array probe is arranged to transmit a push pulse along a predetermined vector so as to generate a shear wave,
wherein the ultrasonic array probe is arranged to transmit tracking pulses along tracking lines adjacent to the push pulse vector,
wherein the ultrasonic array probe is arranged to receive echoes from points along the tracking lines;
a beamformer that is coupled to the ultrasonic array probe, wherein the beamformer is configured to receive echoes along the tracking lines in a time-interleaved sequence,
wherein the beamformer is arranged to convert the echoes to echo data;
an A-line memory arranged to store the echo data; and a processor circuit arranged for background motion compensation based solely on the tracking pulse-related echo data,
  wherein the processor circuit is arranged to compensate for effects of background motion on the echo data by spatially high pass filtering pulse-to-pulse autocorrelation phases of the tracking pulse-related echo data.

2. The ultrasonic diagnostic imaging system of claim 1, wherein the processor circuit is arranged to measure a velocity of a shear wave passing through tracking line locations,
  wherein the measurement of the velocity of the shear wave is based on echo data that has been compensated for the effects of background motion.

3. The ultrasonic diagnostic imaging system of claim 1, wherein the processor circuit is arranged to perform complex autocorrelation of the echo data.

4. The ultrasonic diagnostic imaging system of claim 1, wherein the processor circuit is arranged to operate at each tracking pulse repetition interval.

5. The ultrasonic diagnostic imaging system of claim 2, further comprising a display arranged to display results of a shear wave measurement.

6. The ultrasonic diagnostic imaging system of claim 5, wherein the display is further arranged to display a map of shear wave velocity.

7. The ultrasonic diagnostic imaging system of claim 1, wherein the beamformer comprises a multiline beamformer arranged to detect echo signals along a plurality of tracking line locations in response to a single tracking pulse transmit event.

8. The ultrasonic diagnostic imaging system of claim 1, wherein the processor circuit is arranged to detect a time of peak tissue displacement at a plurality of sample points along each of the tracking line locations.

9. The ultrasonic diagnostic imaging system of claim 1, wherein the processor circuit is arranged to perform lag-1 autocorrelation of complex echo data each pulse repetition interval.

10. The ultrasonic diagnostic imaging system of claim 9, wherein the processor circuit is arranged to perform lag-1 autocorrelation on an ensemble of complex echo data.

11. The ultrasonic diagnostic imaging system of claim 10, further comprising a summer configured to compute a spatial sum value of an autocorrelation result over the two-dimensional region of a tracking line region-of-interest.

12. An ultrasonic diagnostic imaging system comprising:
  an ultrasonic array probe,
  wherein the ultrasonic array probe is arranged to transmit a push pulse along a predetermined vector so as to generate a shear wave,
  wherein the ultrasonic array probe is arranged to transmit tracking pulses along tracking lines adjacent to the push pulse vector,
  wherein the ultrasonic array probe is arranged to receive echoes from points along the tracking lines;
  a beamformer that is coupled to the ultrasonic array probe,
  wherein the beamformer is configured to receive echoes along the tracking lines in a time-interleaved sequence,
  wherein the beamformer is arranged to convert the echoes to echo data;
  an A-line memory arranged to store the echo data; and
  a processor circuit arranged for background motion compensation based on the echo data,
  wherein the processor circuit is arranged to compensate for effects of background motion on the echo data by spatially high pass filtering pulse-to-pulse autocorrelation phases of echo data,
  wherein the processor circuit is arranged to perform lag-1 autocorrelation of complex echo data each pulse repetition interval,
  wherein the processor circuit is arranged to perform lag-1 autocorrelation on an ensemble of complex echo data, and
  wherein the processor circuit is arranged to convert spatial sum values to conjugate unit phasor values.

13. The ultrasonic diagnostic imaging system of claim 12, wherein the processor circuit is arranged to multiply lag-1 autocorrelation data with conjugate unit phasor values to provide background motion compensated data.

14. The ultrasonic diagnostic imaging system of claim 13, wherein the processor circuit is arranged to compute an arc tangent of background motion compensated data.

15. The ultrasonic diagnostic imaging system of claim 14, wherein the computed arc tangent of background motion compensated data further comprises a measure of tissue displacement.

* * * * *